(12) United States Patent
Appenrodt et al.

(10) Patent No.: US 8,734,466 B2
(45) Date of Patent: May 27, 2014

(54) METHOD AND APPARATUS FOR CONTROLLED INSERTION AND WITHDRAWAL OF ELECTRODES

(75) Inventors: Peter Appenrodt, Bremen (DE); Frans L. H. Gielen, Eckelrade (NL)

(73) Assignee: Medtronic, Inc., Minneapolis, MN (US)

( * ) Notice: Subject to any disclaimer, the term of this patent is extended or adjusted under 35 U.S.C. 154(b) by 1097 days.

(21) Appl. No.: 11/739,791

(22) Filed: Apr. 25, 2007

(65) Prior Publication Data

US 2008/0269777 A1 Oct. 30, 2008

(51) Int. Cl.
*A61B 19/00* (2006.01)
*A61N 1/05* (2006.01)

(52) U.S. Cl.
CPC ........... *A61B 19/201* (2013.01); *A61B 19/5244* (2013.01); *A61N 1/0529* (2013.01)
USPC .......................................... 606/129; 606/130

(58) Field of Classification Search
CPC . A61N 1/0526; A61N 1/0529; A61N 1/0531; A61N 1/0534; A61N 1/0539; A61N 1/0587; A61N 1/056; A61N 2001/0578; A61B 5/04001; A61B 5/0478; A61B 5/0492; A61B 5/6848; A61B 5/685; A61B 19/201; A61B 19/5244
USPC .......... 606/129, 130, 108; 604/506, 508, 510, 604/512; 607/6, 7, 115, 116, 117, 148, 45; 600/373, 377, 378
See application file for complete search history.

(56) References Cited

U.S. PATENT DOCUMENTS

| | | |
|---|---|---|
| 5,370,118 A | 12/1994 | Vij et al. |
| 5,570,182 A | 10/1996 | Nathel et al. |
| 5,577,503 A | 11/1996 | Bonutti |
| 5,592,939 A | 1/1997 | Martinelli |
| 5,676,673 A | 10/1997 | Ferre et al. |
| 5,682,890 A | 11/1997 | Kormos et al. |
| 5,740,808 A | 4/1998 | Panescu et al. |
| 5,762,064 A | 6/1998 | Polvani |
| 5,772,594 A | 6/1998 | Barrick |

(Continued)

FOREIGN PATENT DOCUMENTS

| | | |
|---|---|---|
| EP | 1743591 | 1/2007 |
| FR | 2798295 | 3/2001 |

(Continued)

OTHER PUBLICATIONS

Johnson, Jennie et al., "Independently movable multielectrode array to record multiple fast-spiking neurons in the cerebral cortex during cognition" Methods, vol. 30, 2003, pp. 64-78, XP002465099 sections 2.2., 3.2; figures 1,2.

(Continued)

*Primary Examiner* — Ryan Severson
*Assistant Examiner* — David Eastwood
(74) *Attorney, Agent, or Firm* — Harness, Dickey & Pierce, PLC

(57) ABSTRACT

A system for a controlled insertion and withdrawal of at least one electrode in the anatomy. The system can include a guide device and at least one electrode located within the guide device to at least one of record or stimulate an anatomy. The system can also include an indicator coupled to the electrode to indicate a position of a distal end of an electrode relative to the guide device.

17 Claims, 7 Drawing Sheets

(56) References Cited

U.S. PATENT DOCUMENTS

| | | | |
|---|---|---|---|
| 5,868,675 A | 2/1999 | Henrion et al. | |
| 5,871,445 A | 2/1999 | Bucholz | |
| 5,913,820 A | 6/1999 | Bladen et al. | |
| 5,938,599 A | 8/1999 | Rasche et al. | |
| 5,983,126 A | 11/1999 | Wittkampf et al. | |
| 6,006,126 A | 12/1999 | Cosman | |
| 6,011,996 A * | 1/2000 | Gielen et al. | 607/116 |
| 6,015,406 A | 1/2000 | Goble et al. | |
| 6,033,415 A | 3/2000 | Mittelstadt et al. | |
| 6,078,841 A | 6/2000 | Kuzma | |
| 6,084,411 A | 7/2000 | Giaquinto et al. | |
| 6,106,464 A | 8/2000 | Bass et al. | |
| 6,117,143 A | 9/2000 | Hynes et al. | |
| 6,122,541 A | 9/2000 | Cosman et al. | |
| 6,195,580 B1 | 2/2001 | Grable | |
| 6,205,411 B1 | 3/2001 | DiGioia, III et al. | |
| 6,235,038 B1 | 5/2001 | Hunter et al. | |
| 6,246,900 B1 | 6/2001 | Cosman et al. | |
| 6,273,896 B1 | 8/2001 | Franck et al. | |
| 6,301,492 B1 * | 10/2001 | Zonenshayn | 600/378 |
| 6,311,082 B1 | 10/2001 | Creighton, IV et al. | |
| 6,351,662 B1 | 2/2002 | Franck et al. | |
| 6,368,329 B1 | 4/2002 | Truwit | |
| 6,381,485 B1 | 4/2002 | Hunter et al. | |
| 6,405,072 B1 | 6/2002 | Cosman | |
| 6,413,263 B1 * | 7/2002 | Lobdill et al. | 606/129 |
| 6,474,341 B1 | 11/2002 | Hunter et al. | |
| 6,477,400 B1 | 11/2002 | Barrick | |
| 6,482,182 B1 | 11/2002 | Carroll et al. | |
| 6,490,475 B1 | 12/2002 | Seeley et al. | |
| 6,491,699 B1 | 12/2002 | Henderson et al. | |
| 6,493,573 B1 | 12/2002 | Martinelli et al. | |
| 6,516,212 B1 | 2/2003 | Bladen et al. | |
| 6,529,765 B1 | 3/2003 | Franck et al. | |
| 6,546,277 B1 | 4/2003 | Franck et al. | |
| 6,606,521 B2 | 8/2003 | Paspa et al. | |
| 6,618,612 B1 | 9/2003 | Acker et al. | |
| 6,662,036 B2 | 12/2003 | Cosman | |
| 6,704,957 B2 | 3/2004 | Rhodes | |
| 6,752,812 B1 | 6/2004 | Truwit | |
| 6,826,423 B1 | 11/2004 | Hardy et al. | |
| 6,829,508 B2 | 12/2004 | Schulman et al. | |
| 6,847,849 B2 | 1/2005 | Mamo et al. | |
| 6,862,805 B1 | 3/2005 | Kuzma et al. | |
| 6,896,675 B2 | 5/2005 | Leung et al. | |
| 7,033,326 B1 * | 4/2006 | Pianca et al. | 600/585 |
| 7,130,676 B2 | 10/2006 | Barrick | |
| 7,177,701 B1 | 2/2007 | Pianca | |
| 7,206,627 B2 | 4/2007 | Abovitz et al. | |
| 7,217,276 B2 | 5/2007 | Henderson et al. | |
| 7,235,084 B2 | 6/2007 | Skakoon et al. | |
| 7,313,430 B2 | 12/2007 | Urquhart et al. | |
| 7,619,416 B2 | 11/2009 | Nordmeyer-Massner et al. | |
| 7,747,312 B2 | 6/2010 | Barrick et al. | |
| 7,751,865 B2 | 7/2010 | Jascob et al. | |
| 8,597,338 B2 * | 12/2013 | Carpentier | 607/89 |
| 2001/0011175 A1 | 8/2001 | Hunter et al. | |
| 2001/0014820 A1 * | 8/2001 | Gielen et al. | 607/116 |
| 2001/0034530 A1 | 10/2001 | Malackowski et al. | |
| 2002/0042619 A1 | 4/2002 | Dominguez et al. | |
| 2002/0072737 A1 * | 6/2002 | Belden et al. | 606/34 |
| 2002/0087101 A1 | 7/2002 | Barrick et al. | |
| 2002/0111634 A1 * | 8/2002 | Stoianovici et al. | 606/129 |
| 2002/0183608 A1 | 12/2002 | Marmulla et al. | |
| 2003/0009207 A1 | 1/2003 | Paspa et al. | |
| 2003/0078569 A1 | 4/2003 | Caldera et al. | |
| 2003/0097061 A1 | 5/2003 | Ferre et al. | |
| 2003/0114752 A1 | 6/2003 | Henderson et al. | |
| 2003/0163040 A1 * | 8/2003 | Gildenberg | 600/429 |
| 2003/0187351 A1 | 10/2003 | Franck et al. | |
| 2004/0092815 A1 | 5/2004 | Schweikard et al. | |
| 2004/0147839 A1 | 7/2004 | Moctezuma de la Barrera et al. | |
| 2004/0147851 A1 | 7/2004 | Bignall | |
| 2004/0199072 A1 | 10/2004 | Sprouse et al. | |
| 2004/0215071 A1 | 10/2004 | Frank et al. | |
| 2005/0049486 A1 | 3/2005 | Urquhart et al. | |
| 2005/0075649 A1 | 4/2005 | Bova et al. | |
| 2005/0085714 A1 | 4/2005 | Foley et al. | |
| 2005/0085715 A1 | 4/2005 | Dukesherer et al. | |
| 2005/0085720 A1 | 4/2005 | Jascob et al. | |
| 2005/0119587 A1 | 6/2005 | Roessler et al. | |
| 2005/0198849 A1 | 9/2005 | Goeggelmann et al. | |
| 2005/0226377 A1 | 10/2005 | Wong et al. | |
| 2006/0058683 A1 | 3/2006 | Chance | |
| 2006/0190054 A1 * | 8/2006 | Malinowski et al. | 607/45 |
| 2006/0212044 A1 | 9/2006 | Bova et al. | |
| 2006/0241406 A1 | 10/2006 | Noujeim | |
| 2006/0253181 A1 | 11/2006 | Schulman et al. | |
| 2007/0015991 A1 | 1/2007 | Fu et al. | |
| 2007/0027385 A1 * | 2/2007 | Brister et al. | 600/365 |
| 2007/0167722 A1 | 7/2007 | Bladen et al. | |
| 2008/0204021 A1 | 8/2008 | Leussler et al. | |
| 2008/0269599 A1 | 10/2008 | Csavoy et al. | |
| 2008/0269600 A1 | 10/2008 | Csavoy et al. | |
| 2008/0269602 A1 | 10/2008 | Csavoy et al. | |
| 2009/0012509 A1 | 1/2009 | Csavoy et al. | |
| 2009/0261828 A1 | 10/2009 | Nordmeyer-Massner et al. | |
| 2010/0160771 A1 | 6/2010 | Gielen et al. | |
| 2010/0168826 A1 * | 7/2010 | Carpentier | 607/116 |

FOREIGN PATENT DOCUMENTS

| | | |
|---|---|---|
| GB | 2352512 | 1/2001 |
| WO | WO-9608209 | 3/1996 |
| WO | WO-9611624 A2 | 4/1996 |
| WO | WO-9833451 | 8/1998 |
| WO | WO-0050859 | 8/2000 |
| WO | WO-0224094 | 3/2002 |
| WO | WO-2004044612 | 5/2004 |
| WO | WO-2004100767 | 11/2004 |
| WO | WO-2005039386 | 5/2005 |
| WO | WO-2007002926 | 1/2007 |
| WO | WO-2008036050 | 3/2008 |

OTHER PUBLICATIONS

Communication Relating to the Results of the Partial International Search for PCT/US2007/010164 included as part of Invitation to Pay Additional Fees mailed Feb. 21, 2008.

International Search Report and Written Opinion for PCT/US2007/010164 mailed May 30, 2008.

"microTargeting Drive System for Stereotactice Positioning" FHC, Inc., Mar. 2006.

"Nexframe," 2 sheets printed from www.igneurologics.com on Jul. 9, 2007.

"3M Surgical Drapes, Drape Selection Guide," brochure, 3M copyright 2002, 2003, 2005.

"Fazer® Contour Laser," 9730732, rev. 3 Aug. 2006. 9 Sheets.

"microTargeting® Drive System for Stereotactic Positioning," User Manual L011-1006B, Mar. 2006.

"Navigus, NexFrame, StimLoc", IGN—Image Guided Neurologics, copyright 2004, printed from www.igneurologics.com on Jul. 9, 2007, (2 sheets).

"NeuroNav™," *Alpha Omega Defining Neuroscience Technology*, http://www.alphaomega-eng.com/pr_site/neuronav/index.htm, Web. accessed Apr. 1, 2010.

"NexDrive™ Micro-Positioner, Microelectrode Recording & DBS™ Electrode Implantation," Medtronic, Inc. copyright 2006. (2 sheets).

"Nexframe Reticle System, Trajectory Orientation," Medtronic, Inc. copyright 2006. (2 sheets).

"NexFrame System—Case: Bilateral Activa Lead Delivery to STN Using Nexframe," IGN Image Guided Neurologics, Inc. copyright 2004. Printed from www.igneurologics.com on Jul. 9, 2007. (2 sheets).

"Passive Headrest, Full Head and Neck Support," Medtronic, Inc. copyright 2006, (2 sheets).

"Stimloc™ Lead Securement Device," Medtronic, Inc. 2006. (2 sheets).

"The DBS Solution, Enabling Technologies, Case Studies," Medtronic, Inc. copyright 2006.

(56) References Cited

OTHER PUBLICATIONS

"The NexFrame System, Stereotactic Technology," Medtronic, Inc. copyright 2006. (3 sheets).
"Trace™ Registration Feature", 9731369, rev. 2 Sep. 2004. 3 sheets.
"Unibody™ Fiducials, Unibody Fiducial Marker," Medtronic, Inc. copyright 2006, (2 sheets).
International Preliminary Report on Patentability and Written Opinion for PCT/US2007/009928 mailed Nov. 5, 2009 claiming benefit of U.S. Appl. No. 11/739,401, filed Apr. 24, 2007.
International Preliminary Report on Patentability and Written Opinion for PCT/US2007/010121 issued Oct. 27, 2009 claiming benefit of U.S. Appl. No. 11/739,424, filed Apr. 24, 2007.
International Preliminary Report on Patentability and Written Opinion for PCT/US2007/010164 mailed Nov. 5, 2009 claiming benefit of U.S. Appl. No. 11/739,791, filed Apr. 25, 2007.
International Search Report and Written Opinion for case PCT/US2008/060316 mailed Jul. 11, 2008.
International Search Report and Written Opinion for PCT/US2007/009928 mailed on Mar. 26, 2008.
International Search Report and Written Opinion for PCT/US2007/010121 mailed Jan. 24, 2008.
International Search Report and Written Opinion for PCT/US2007/010164 mailed May 30, 2008 claiming benefit of U.S. Appl. No. 11/739,791, filed Apr. 25, 2007.
International Search Report and Written Opinion for PCT/US2008/082961 mailed Mar. 3, 2009 claiming benefit of U.S. Appl. No. 12/110,666, filed Apr. 28, 2008, which claims priority to U.S. Appl. No. 11/739,401, filed Apr. 24, 2007.
Rosenow, Joshua, "Application Accuracy of an Electromagnetic Field-Based Image-Guided Navigation System,"Stereotactic Fuct Neurosurg 2007; 85:75-81, Dec. 12, 2006.
Final Office Action mailed Oct. 14, 2011 for U.S. Appl. No. 12/062,605.
Interview Summary mailed Aug. 18, 2011 for U.S. Appl. No. 12/062,605.
Notice of Allowance mailed Sep. 14, 2011 for U.S. Appl. No. 11/739,424.
Office Communication and Issue Classification mailed Oct. 7, 2011 for U.S. Appl. No. 11/739,424.

* cited by examiner

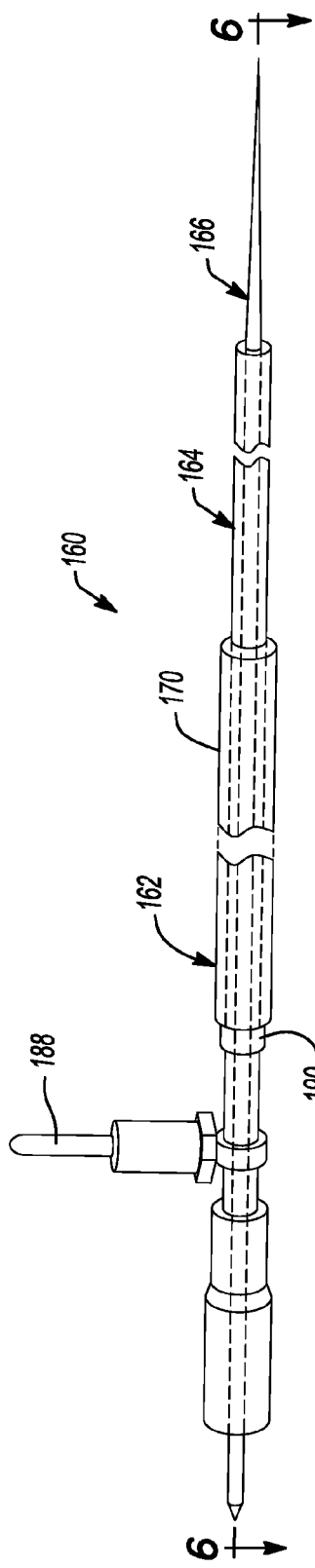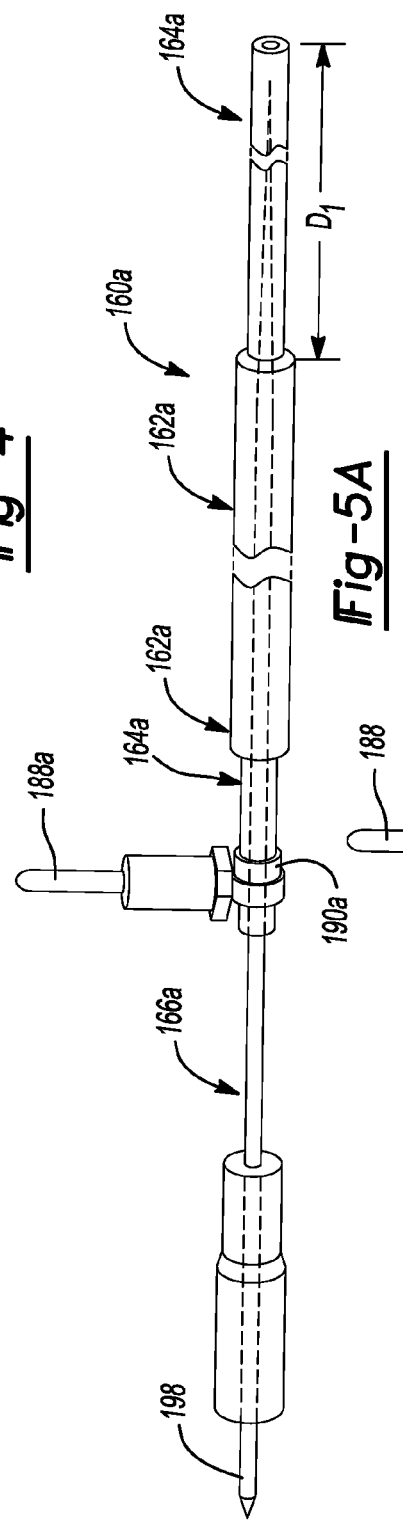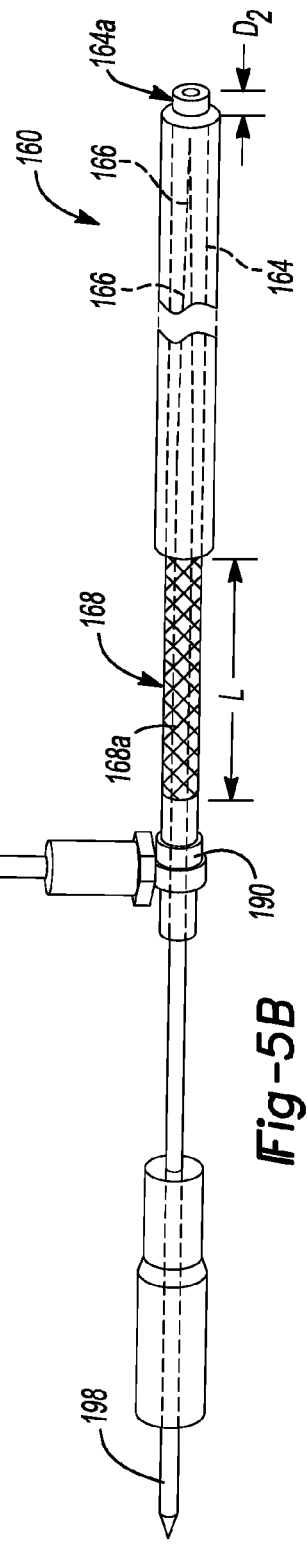

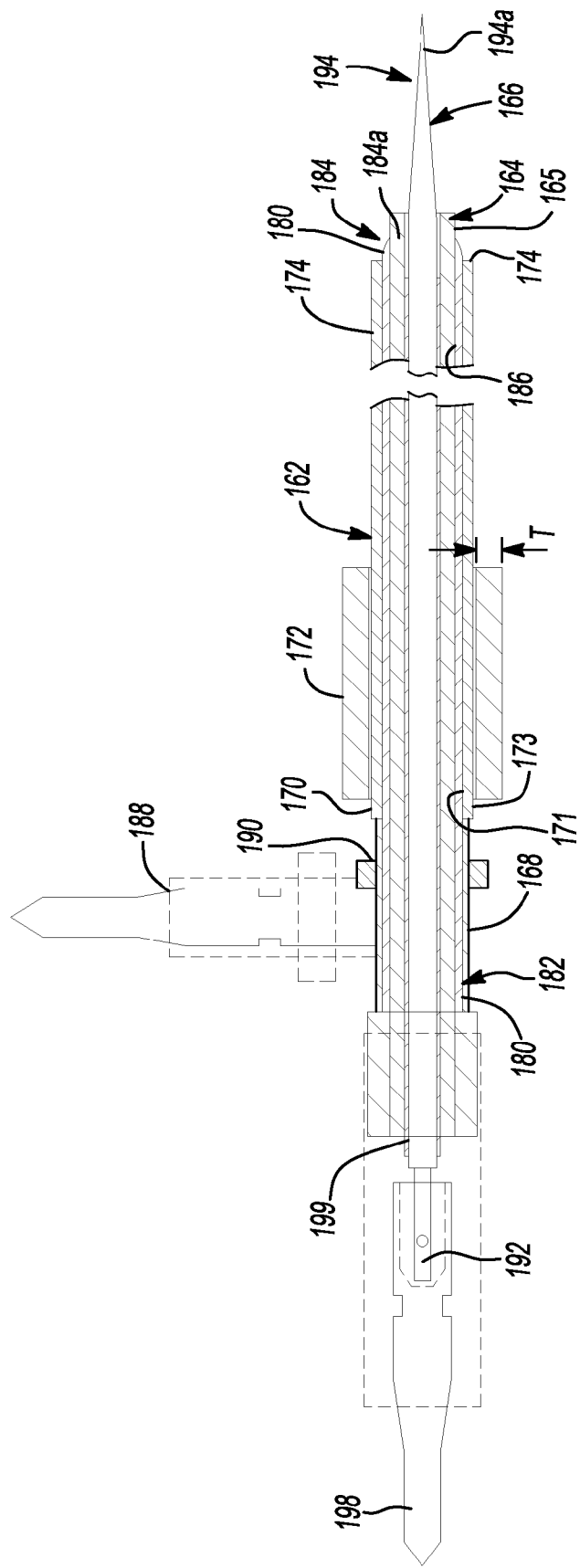

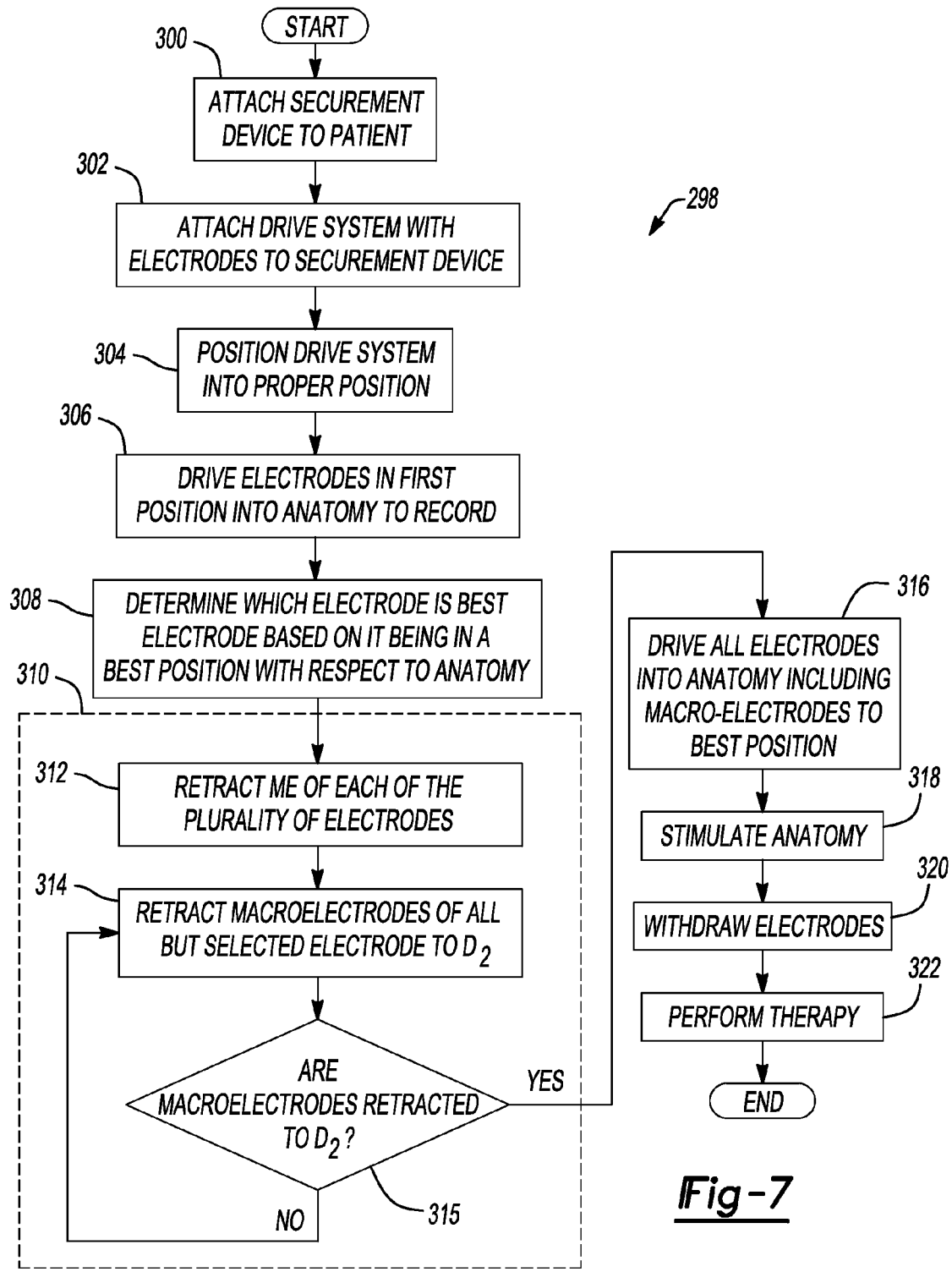

METHOD AND APPARATUS FOR CONTROLLED INSERTION AND WITHDRAWAL OF ELECTRODES

FIELD

The present disclosure relates generally to a neurosurgical procedure, and more specifically, to methods and apparatuses for the controlled insertion and withdrawal of test electrodes during a neurosurgical procedure.

BACKGROUND

The statements in this section merely provide background information related to the present disclosure and may not constitute prior art.

A surgical procedure can be performed on various portions of an anatomy, such as a human anatomy. The surgical procedures can be invasive to varying degrees, such as by performing an open procedure or by performing a less invasive procedure. A procedure can be performed in a less invasive manner by minimizing or attempting to minimize an incision or portal formed in the tissue of the anatomy, opening through bone, and other minimization techniques.

A less invasive procedure, however, can also reduce visualization of a portion of the anatomy upon which a procedure is occurring, reduce access with various instruments to a portion of the anatomy, and the like. The less invasive procedure may also require specialized and particular instruments to perform the procedure in an appropriate and beneficial manner. It is desirable, therefore, to provide instruments, procedures, and the like to achieve an optimal outcome while maintaining the less invasive procedure.

Instruments, according to various applications, can be guided with exterior guide tools or systems to a selected portion of the anatomy to perform the procedure in the less invasive manner. For example, a scope can be guided along a selected portion of the anatomy for viewing an internal structure within the anatomy. Various other instruments can also be guided into the anatomy for various procedures. For example, a microelectrode (ME) for recording can be guided into a portion of the anatomy, such as the brain, to record electrical activity therein. The recording of the electrical activity can be used for various diagnoses and identification procedures. A probe or deep brain stimulation (DBS) or macroelectrode stimulation probe can then be guided in an area relative to the ME.

SUMMARY

A system for a controlled insertion and withdrawal of at least one electrode in the anatomy. The system can include a guide device and at least one electrode located within the guide device to at least one of record or stimulate an anatomy. The system can also include an indicator coupled to the electrode to indicate a position of a distal end of the at least one electrode relative to the guide device.

According to various embodiments, a system can be used to both record and stimulate a portion of the anatomy, such as the brain. The recording portion can be positioned within a stimulation portion and both positioned with a guiding member or through passage member and inserted into the brain to a selected position. A specific or selected region within the brain can be selected to be stimulated based upon recordings with the recording portion. An array of the recording portions and stimulation portions can be positioned in the brain, while a single one is to be used to stimulate the selected region. Therefore, all but one of the array of the recording and stimulation portions can be withdrawn or extracted to a selected position as the array is driven or moved further into the brain. This can allow a selected or minimum amount of material to be positioned into the selected specific region of the brain. Thus, a system is disclosed that can selectively limit or position only a selected amount of material into a specific region of the brain.

Further provided is a system for controlled insertion and withdrawal of at least one electrode in an anatomy. The system can include at least one insertion cannula that defines a first bore and a distal end and a macroelectrode slideably coupled in the first bore. The macroelectrode can have a proximal end and a distal end that is selectively extendable beyond the distal end of the at least one insertion cannula to engage the anatomy. The macroelectrode can define a second bore. The system can also include a microelectrode slideably coupled in the second bore. The microelectrode can have a proximal end and a distal end, and the distal end can be selectively extendable beyond the distal end of the macroelectrode to engage the anatomy. The system can comprise at least one indicator operable to indicate the position of the distal end of one of the macroelectrode and the microelectrode relative to the distal end of the at least one insertion cannula.

A system for the controlled insertion and withdrawal of at least one electrode is provided. The system can include a cannulated electrode assembly. The cannulated electrode assembly can include at least one insertion cannula and at least one electrode slideably coupled to a first bore defined in the at least one insertion cannula. The at least one electrode can be selectively extendable beyond a distal end of the at least one insertion cannula. The system can also include a drive system coupled to the at least one insertion cannula to move one of the at least one insertion cannula or the at least one electrode into an anatomy. The system can comprise a guide system to the anatomy and the drive system to enable a desired orientation of the drive system relative to the anatomy. The system can also include an indicator coupled to the at least one electrode that indicates the position of the at least one electrode with respect to the at least one insertion cannula.

Further provided is a method of controlling the insertion and withdrawal of at least one electrode from an anatomy. The method can include positioning at least one electrode in a guide device and guiding the at least one electrode to a first position in the anatomy. The method can also include guiding the at least one electrode to a second position in an anatomy, and viewing an indicator coupled to the at least one electrode to confirm the at least one electrode is in the second position.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4 is a perspective view of one of the exemplary test electrodes of the present disclosure in a first position;

FIG. 5A is a perspective view of a second position for a selected one of the exemplary test electrodes;

FIG. 5B is a perspective view of a second position for a remainder of the exemplary test electrodes;

FIG. 6 is a cross-sectional view of one of the exemplary test electrodes taken along line 6-6 of FIG. 4, but illustrating the test electrode in a fully retracted position;

FIG. 7 is a flow chart illustrating an exemplary procedure for a controlled insertion and withdrawal of employing the test electrodes.

DETAILED DESCRIPTION

Figure 1:
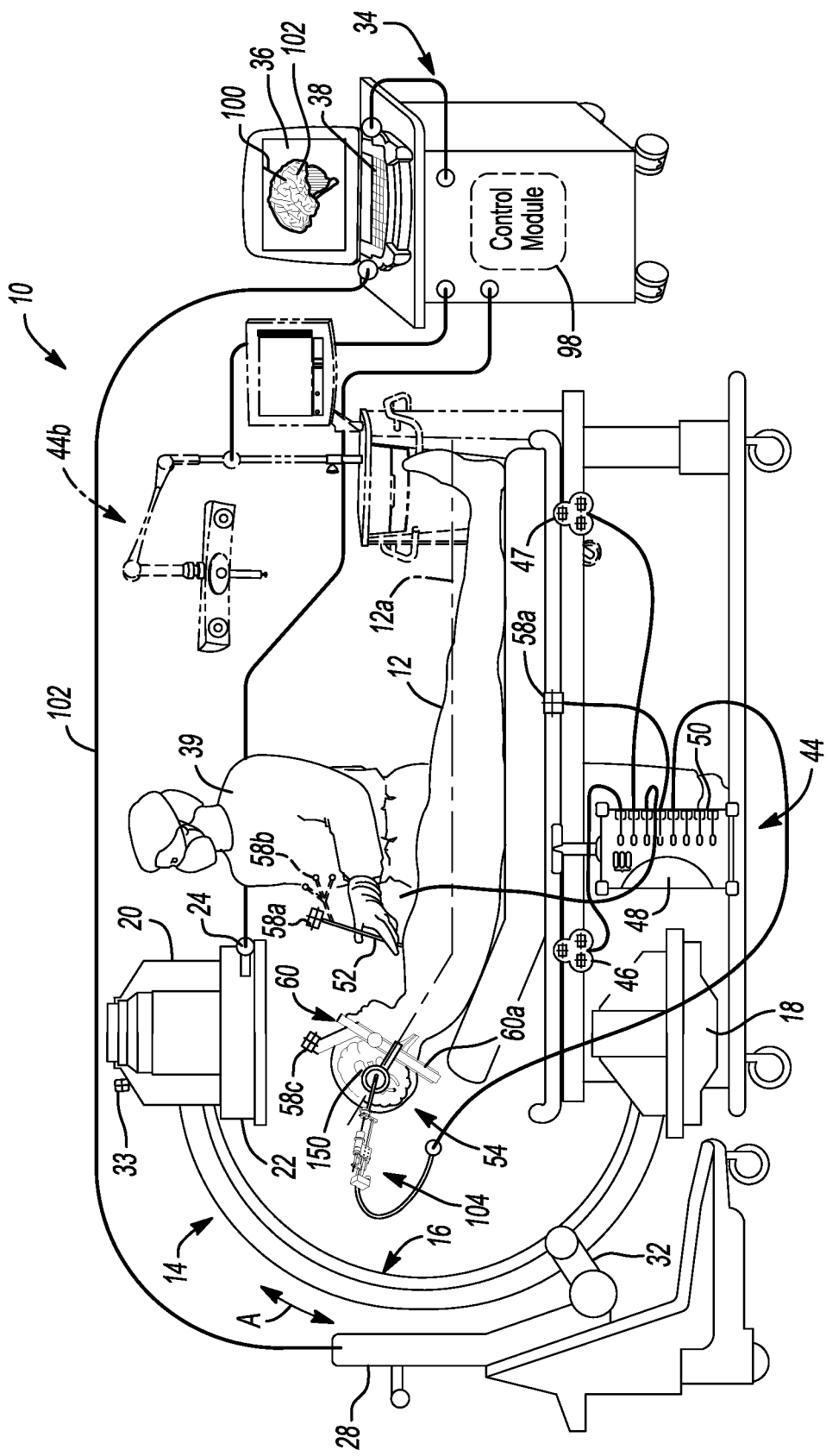
FIG. 1 is a diagram of a navigation system according to various embodiments of the present disclosure.

The following description is merely exemplary in nature and is not intended to limit the present disclosure, application, or uses. It should be understood that throughout the drawings, corresponding reference numerals indicate like or corresponding parts and features. As indicated above, the present teachings are directed toward providing a system and method for the controlled insertion and withdrawal of one or more test electrodes during a surgical procedure. It should be noted, however, that the present teachings could be applicable to other appropriate procedures. Therefore, it will be understood that the following discussions are not intended to limit the scope of the appended claims.

As will be discussed in greater detail herein, the present disclosure is directed toward a system and method for the controlled insertion and withdrawal of electrodes from an anatomy, such as a brain. This system and method can include the use of a drive system 104 to control the insertion and withdrawal of one or more cannulated electrodes 160 from the anatomy. The drive system 104 and the cannulated electrodes 160 can be used in an operating theater, including an exemplary surgical navigation system 10, as illustrated in FIG. 1. Various surgical navigation systems can include those described in U.S. patent application Ser. No. 10/651,267 (now U.S. Pat. App. Pub No. 2005/0049486), filed on Aug. 28, 2003, incorporated herein by reference.

The exemplary surgical navigation system 10 can include an image based system, an imageless system, an atlas or diagram based system, or combinations thereof. One skilled in the art will understand that the surgical navigation system 10 can require the registration of the patient 12, which defines patient space, to a tracking system, discussed further herein. According to various embodiments, registration can include registration between image space, defined by image data or atlas data, and the patient space. It will be understood, however, that surgical navigation system 10, as discussed with regard to FIG. 1, is merely optional, and any appropriate technique and/or system could be used to control the insertion and withdrawal of the cannulated electrodes 160, such as a robotic arm, stereotactic head frame, etc. Thus, it will be understood that the foregoing discussion of the exemplary navigation system 10 will not limit the appended claims to require a navigation system or a tracking system, as disclosed herein.

With reference to FIG. 1, a navigation system 10 that can be used for various procedures is illustrated. The navigation system 10 can be used to track the location of a imaging device 14, such as a pointer probe, relative to a patient 12 to assist in the implementation or performance of a surgical procedure. It should be further noted that the navigation system 10 may be used to navigate or track other devices including: catheters, probes, needles, leads, implants, etc. According to various embodiments, examples include ablation catheters, deep brain stimulation (DBS) or macro-electrodes or leads, micro-electrodes (ME) or leads for recording, etc. Moreover, the navigated device may be used in any region of the body. The navigation system 10 and the various devices may be used in any appropriate procedure, such as one that is generally minimally invasive, arthroscopic, percutaneous, stereotactic, or an open procedure. Although an exemplary navigation system 10 including an imaging device 14 are discussed herein, one skilled in the art will understand that the disclosure is merely for clarity of the present discussion and any appropriate imaging system, navigation system, patient specific data, and non-patient specific data can be used. For example, the intraoperative imaging system can include an MRI imaging system, such as the PoleStar® MRI sold by Medtronic, Inc. or a X-ray imaging system including the O-ARM® imaging system sold by Breakaway Imaging, LLC. having a place of business in Massachusetts, USA. It will be understood that the navigation system 10 can incorporate or be used with any appropriate preoperatively or intraoperatively acquired image data.

The navigation system 10 may include an imaging device 14 that is used to acquire pre-, intra-, or post-operative or real-time image data of the patient 12. Alternatively various imageless systems can be used or images from atlas models can be used to produce patient images, such as those disclosed in U.S. Patent Pub. No. 2005-0085714, filed Oct. 16, 2003, entitled "METHOD AND APPARATUS FOR SURGICAL NAVIGATION OF A MULTIPLE PIECE CONSTRUCT FOR IMPLANTATION," incorporated herein by reference. The imaging device 14 can be, for example, a fluoroscopic x-ray imaging device that may be configured as the O-ARM® imaging device or a C-arm 16 having an x-ray source 18, an x-ray receiving section 20, an optional calibration and tracking target 22 and optional radiation sensors 24. It will be understood, however, that patient image data can also be acquired using other imaging devices, such as those discussed above and herein.

An imaging device controller 28, that can control the C-arm 16, can capture the x-ray images received at the x-ray receiving section 20 and store the images for later use. The controller 28 may also be separate from the C-arm 16 and/or control the rotation of the C-arm 16. For example, the C-arm 16 can move in the direction of arrow A or rotate about a longitudinal axis 12a of the patient 12, allowing anterior or lateral views of the patient 12 to be imaged. Each of these movements involves rotation about a mechanical axis 32 of the C-arm 16. The movements of the imaging device 14, such as the C-arm 16 can be tracked with a tracking device 33.

In the example of FIG. 1, the longitudinal axis 12a of the patient 12 is substantially in line with the mechanical axis 32 of the C-arm 16. This can enable the C-arm 16 to be rotated relative to the patient 12, allowing images of the patient 12 to be taken from multiple directions or about multiple planes. An example of a fluoroscopic C-arm X-ray device that may be used as the optional imaging device 14 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc. The O-ARM® imaging device is available from Breakaway Imaging, LLC of Littleton, Mass.

Two dimensional fluoroscopic images that may be taken by the imaging device 14 are captured and stored in the controller 28 as patient image data 102. The patient image data 102 can then be forwarded from the controller 28 to a navigation computer and/or processor or workstation 34. It will also be understood that the image data is not necessarily first retained in the controller 28, but may also be directly transmitted to the workstation 34. The workstation 34 can include a display 36, a user input device 38 and a control module 98. The workstation 34 can also include or be connected to an image processor, navigation processor, and memory to hold instruction and data. The workstation 34 provides facilities for displaying the patient image data 102 as an image on the display 36, saving, digitally manipulating, or printing a hard copy image of the received patient image data 102. The user input device 38 can comprise any device, such as an user input device 38, that can enable a user to interface with the workstation 34, such as a touchpad, touch pen, touch screen, keyboard, mouse, wireless mouse, or a combination thereof. The user input device 38 allows a physician or user 39 to provide inputs to control the imaging device 14, via the C-arm controller 28, or adjust the display settings of the display 36.

The control module 98 can determine the location of the various instruments 52 with respect to the patient space, and can output image data 99 to the display 36 as will be discussed herein. The image data 99 can comprise an icon 100 that provides an indication of the location of the instruments with respect to the patient space, illustrated on the patient image data 102. It should be noted that the patient image data 102 can comprise at least one of data from the navigation system 10, image data acquired by the imaging device 14, patient information entered by the user through the user input device 38, pre-operative images, or combinations thereof.

While the optional imaging device 14 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), optical coherence tomography (OCT) (a more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference). Intra-vascular ultrasound (IVUS), intra-operative CT, single photo emission computed tomography (SPECT), planar gamma scintigraphy (PGS). Addition imaging systems include intraoperative MRI systems such as the PoleStar® MRI system sold by Medtronic, Inc. Further systems include the O-ARM® imaging system sold by Breakaway Imaging, LLC. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sites within the patient 12. It should further be noted that the imaging device 14, as shown in FIG. 1, provides a virtual bi-plane image using a single-head C-arm fluoroscope as the imaging device 14 by simply rotating the C-arm 16 about at least two planes, which could be orthogonal planes, to generate two-dimensional images that can be converted to three-dimensional volumetric images. By acquiring images in more than one plane, the icon 100 representing the location of an impacter, stylet, reamer driver, taps, drill, deep-brain stimulation (DBS) electrodes or probes, or other instrument, introduced and advanced in the patient 12, may be superimposed in more than one view and included in the image data 99 displayed on the display 36.

Four-dimensional (4D) image information can be used with the navigation system 10 as well. For example, the user 39 can use a physiologic signal, which can include Heart Rate (measured with an EKG), Breath Rate (Breath Gating) and combine this data with image data 99 acquired during the phases of the physiologic signal to represent the anatomy of the patient 12 at various stages of the physiologic cycle. For example, with each heartbeat the brain pulses (and therefore moves). Images can be acquired to create a 4D map of the brain, onto which atlas data and representations of a device, such as a surgical instrument can be projected. This 4D data set can be matched and co-registered with the physiologic signal (e.g. EKG) to represent a compensated image within the system. The image data registered with the 4D information can show the brain (or anatomy of interest) moving during the cardiac or breath cycle. This movement can be displayed on the display 36 as the image data 99. Also, the gating techniques can be used to eliminate movement in the image displayed on the display 36.

Likewise, other imaging modalities can be used to gather the 4D dataset to which pre-operative 2D and 3D data can be matched. One need not necessarily acquire multiple 2D or 3D images during the physiologic cycle of interest (breath or heart beat). Ultrasound imaging or other 4D imaging modalities can be used to create an image data that allows for a singular static pre-operative image to be matched via image-fusion techniques and/or matching algorithms that are non-linear to match the distortion of anatomy based on the movements during the physiologic cycle. The combination of a dynamic reference frame 44 and 4D registration techniques can help compensate for anatomic distortions during movements of the anatomy associated with normal physiologic processes.

With continuing reference to FIG. 1, the navigation system 10 can further include a tracking system, such as, but not limited to, an electromagnetic (EM) tracking system 46 or an optical tracking system 46'. Either or both can be used alone or together in the navigation system 10. Moreover, discussion of the EM tracking system 46 can be understood to relate to any appropriate tracking system. The optical tracking system 46' can include the StealthStation® Treon® and the StealthStation® Tria® both sold by Medtronic Navigation, Inc. Other tracking systems include acoustic, radiation, radar, infrared, etc.

The EM tracking system 44 that can include a localizer, such as a coil array 46 and/or second coil array 47, a coil array controller 48, a navigation probe interface 50, a device or instrument 52 (e.g. catheter, ME for recording, macroelectrode stimulators, cannulas, biopsy needles, DBS probes or other instruments, as discussed herein), a dynamic reference frame (DRF) 54 and tracking device 58. The instrument 52 and the DRF 54 can include a tracking device 58 that can be recognized by the tracking system 44.

The tracking device 58 or any appropriate tracking device as discussed herein, can include both a sensor, a transmitter, or combinations thereof. Further, the tracking devices 58 can be wired or wireless to provide a signal or emitter or receive a signal from a system. Nevertheless, a tracking device 58a can include an electromagnetic coil to sense a field produced by the localizing coil array 46 or 47, while a tracking device 58b can include reflectors that can reflect a signal to be received by the optical localizer or optical tracking system 44b. Nevertheless, one will understand that the tracking device 58 can receive a signal, transmit a signal, or combinations thereof to provide information to the navigation system 10 to determine a location of the tracking device 58, 33. The navigation system 10 can then determine a position of the instrument 52 based on the location of the tracking device 58 to allow for navigation relative to the patient 12 in image space.

With regard to the optical localizer or optical tracking system 44b, the optical tracking system 44b can transmit and receive an optical signal, or combinations thereof. An optical tracking device 58b can be interconnected with the instrument 52, or other devices, such as the DRF 54. As is generally known the optical tracking device 58b can reflect, transmit or receive an optical signal to/from the optical localizer or optical tracking system 44b that can be used in the navigation system 10 to navigate or track various elements. Therefore, one skilled in the art will understand, that the tracking devices 33, 58a, and 58b can be any appropriate tracking device to work with any one or multiple tracking systems 44

An EM tracking system 44 can include the coil arrays 46, 47. The coil arrays 46, 47 can be coupled to an operating table 49, however, the coil arrays 46, 47 could be supplemented or replaced with a mobile localizer (not shown). The mobile localizer may be one such as that described in U.S. patent application Ser. No. 10/941,782, filed Sep. 15, 2004, and entitled "METHOD AND APPARATUS FOR SURGICAL NAVIGATION", herein incorporated by reference. As is understood, the coil arrays 46, 47 can transmit signals that are received by the tracking device 33, 58. The tracking device 33, 58 can then transmit or receive signals based upon the transmitted or received signals from or to the array.

Further included in the navigation system 10 may be an isolator circuit or assembly (not specifically shown). The isolator circuit or assembly may be included in a transmission line to interrupt a line carrying a signal or a voltage to the navigation probe interface 50. Alternatively, the isolator circuit included in the isolator box may be included in the navigation probe interface 50, the instrument 52, the DRF 54, the transmission lines coupling the instruments 52, or any other appropriate location. The isolator assembly is operable to isolate any of the instruments or patient coincidence instruments or portions that are in contact with the patient 12 should an undesirable electrical surge or voltage take place.

It should further be noted that the entire EM tracking system 44 or parts of the EM tracking system 44 may be incorporated into the imaging device 14, including the radiation sensors 24, the workstation 34 and the control module 98. Incorporating the EM tracking system 44 can provide an integrated imaging and tracking system. Any combination of these components can also be incorporated into the imaging device 14, which again can include a fluoroscopic C-arm imaging device or any other appropriate imaging device.

The coil arrays 46, 47 are shown attached to the operating table 49. It should be noted, however, that the coil arrays 46, 47 can also be positioned at any other location as well and can also be positioned in the items being navigated. The coil arrays 46, 47 can include a plurality of coils that are each operable to generate distinct electromagnetic fields into the navigation region of the patient 12, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil arrays 46, 47 can be controlled or driven by the coil array controller 48. The coil array controller 48 can drive each coil in the coil arrays 46, 47 in a time division multiplex or a frequency division multiplex manner. In this regard, each coil can be driven separately at a distinct time or all of the coils can be driven simultaneously with each being driven by a different frequency. Upon driving the coils in the coil arrays 46, 47 with the coil array controller 48, electromagnetic fields are generated within the patient 12 in the area where the medical procedure is being performed, which is again sometimes referred to as patient space. The electromagnetic fields generated in the patient space induce currents in a tracking devices 58 positioned on or in the instrument 52. These induced signals from the instrument 52 are delivered to the navigation probe interface 50 and can be subsequently forwarded to the coil array controller 48.

The navigation probe interface 50 may provide all the necessary electrical isolation for the navigation system 10. The navigation probe interface 50 can also include amplifiers, filters and buffers to directly interface with the tracking devices 58 in the instrument 52. Alternatively, the tracking devices 58, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 50.

As discussed, various portions of the navigation system 10, such as the instrument 52, the DRF 54 and others as will be described in detail below, are equipped with at least one, and generally multiple, tracking devices 58, that can also be referred to as localization sensors. The instrument 52 can include a graspable or manipulable portion at a proximal end and the tracking device 58 can be fixed near the manipulable portion of the instrument 52. The instrument 52 may be any appropriate instrument, such as a ME, DBS probe, a macro-electrode stimulation device, etc.

In an alternate embodiment, the electromagnetic sources or generators may be located within the instrument 52, DRF 54, and one or more receiver coils may be provided externally to the patient 12 forming a receiver coil array similar to the coil arrays 46, 47. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The DRF 54 of the tracking system 44 can also be coupled to the navigation probe interface 50 to forward the information to the coil array controller 48. The DRF 54, according to various embodiments, can include a small magnetic field detector. The DRF 54 may be fixed to the patient 12 adjacent to the region being navigated so that any movement of the patient 12 is detected as relative motion between the coil arrays 46, 47 and the DRF 54. This relative motion is forwarded to the coil array controller 48, which updates registration correlation and maintains accurate navigation, further discussed herein. The DRF 54 may include any appropriate tracking device 58 used by the navigation system 10. Therefore the DRF 54 can include an optical tracking device, as indicated by reference number 58b, or acoustic, etc. For example, the DRF 54 can include a DRF holder or head frame 60 and a removable tracking device 58c. Alternatively, the DRF 54 can include a tracking device 58 that can be formed integrally or separately from the head frame 60.

Moreover, the DRF 54 can be provided as separate pieces and can be positioned at any appropriate position on the anatomy. For example, the tracking device 58c of the DRF 54 can be fixed to the skin of the patient 12 with an adhesive. Also, the DRF 54 can be positioned near a leg, arm, etc. of the patient 12. Thus, the DRF 54 does not need to be provided with the head frame 60 or require any specific base or holding portion. If the DRF 54 is used with an electromagnetic tracking device 58a it can be configured as a pair of orthogonally oriented coils, each having the same center or may be configured in any other non-coaxial or co-axial coil configurations (not specifically shown).

Briefly, the navigation system 10 operates as follows. The navigation system 10 creates a translation map between all points in the radiological image generated from the imaging device 14 and the corresponding points in the patient's anatomy in patient space. After this map is established, whenever a tracked instrument, such as the instrument 52 is used, the workstation 34 in combination with the coil array controller 48 and the controller 28 uses the translation map to identify the corresponding point on the pre-acquired image or atlas model, which is displayed on display 36. This identification is known as navigation or localization. The icon 100 representing the localized point or instruments 52 can be shown as image data 99 on the display 36, as will be discussed herein.

To enable navigation, the navigation system 10 must be able to detect both the position of the patient's anatomy and the position of the instrument 52 or attachment member (e.g., tracking device 58) attached to the instrument 52. Knowing the location of these two items allows the navigation system 10 to compute and display the position of the instrument 52 in relation to the patient 12 on the display 36. The tracking system 44 is employed to track the instrument 52 and the anatomy simultaneously.

The tracking system 44, if using an electromagnetic tracking assembly, essentially works by positioning the coil array 46 or coil arrays 46, 47 adjacent to the patient space to generate a low-energy magnetic field generally referred to as a navigation field. Because every point in the navigation field or patient space is associated with a unique field strength, the tracking system 44 can determine the position of the instrument 52 by measuring the field strength at the location of the tracking devices 58. The DRF 54 is fixed to the patient 12 to identify the location of the patient 12 in the navigation field. The tracking system 44 continuously recomputes the relative position of the DRF 54 and the instrument 52 during localization and relates this spatial information to patient registration data to enable image guidance of the instrument 52 within and/or relative to the patient 12.

Patient registration is the process of determining how to correlate the position of the instrument 52 relative to the patient 12 to the position on the diagnostic or pre-acquired images. To register the patient 12, a physician or user 39 may use point registration by selecting and storing particular points from the pre-acquired images and then touching the corresponding points on the patient's anatomy with a pointer probe (not shown). The navigation system 10 analyzes the relationship between the two sets of points that are selected and computes a match, which correlates every point in the image data 99 with its corresponding point on the patient's anatomy or the patient space, as discussed herein. The points that are selected to perform registration are the fiducial markers or markers 64, such as anatomical landmarks. Again, the landmarks or fiducial markers 64 are identifiable on the images and identifiable and accessible on the patient 12. The fiducial markers 64 can be artificial fiducial markers 64 that are positioned on the patient 12 or anatomical landmarks that can be easily identified in the image data 99. The artificial landmarks, such as the fiducial markers 64, can also form part of the DRF 54, such as those disclosed in U.S. Pat. No. 6,381,485, entitled "Registration of Human Anatomy Integrated for Electromagnetic Localization," issued Apr. 30, 2002, herein incorporated by reference.

The navigation system 10 may also perform registration using anatomic surface information or path information as is known in the art. The navigation system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 60/465,615, entitled "Method and Apparatus for Performing 2D to 3D Registration" filed on Apr. 25, 2003, hereby incorporated by reference.

Also as discussed herein, a substantially fiducial-less registration system can be provided, particularly if the imaging device 14 and the tracking system 44 are substantially integrated. Therefore, the tracking system 44 would generally know the position of the imaging device 14 relative to the patient 12 and fiducial markers 64 may not be required to create registration. Nevertheless, it will be understood that any appropriate type of registration system can be provided for the navigation system 10.

In order to maintain registration accuracy, the navigation system 10 continuously tracks the position of the patient 12 during registration and navigation. This is because the patient 12, DRF 54, and coil array 46 may all move during the procedure, even when this movement is not desired. Alternatively the patient 12 may be held immobile once the registration has occurred, such as with the head frame 60. Therefore, if the navigation system 10 did not track the position of the patient 12 or area of the anatomy, any patient movement after image acquisition would result in inaccurate navigation within that image. The DRF 54 allows the tracking system 44 to register and track the anatomy. Because the DRF 54 is rigidly fixed to the patient 12, any movement of the anatomy or the coil array 46 is detected as the relative motion between the coil array 46 and the DRF 54. This relative motion is communicated to the coil array controller 48, via the navigation probe interface 50, which updates the registration correlation to thereby maintain accurate navigation.

Figure 2:
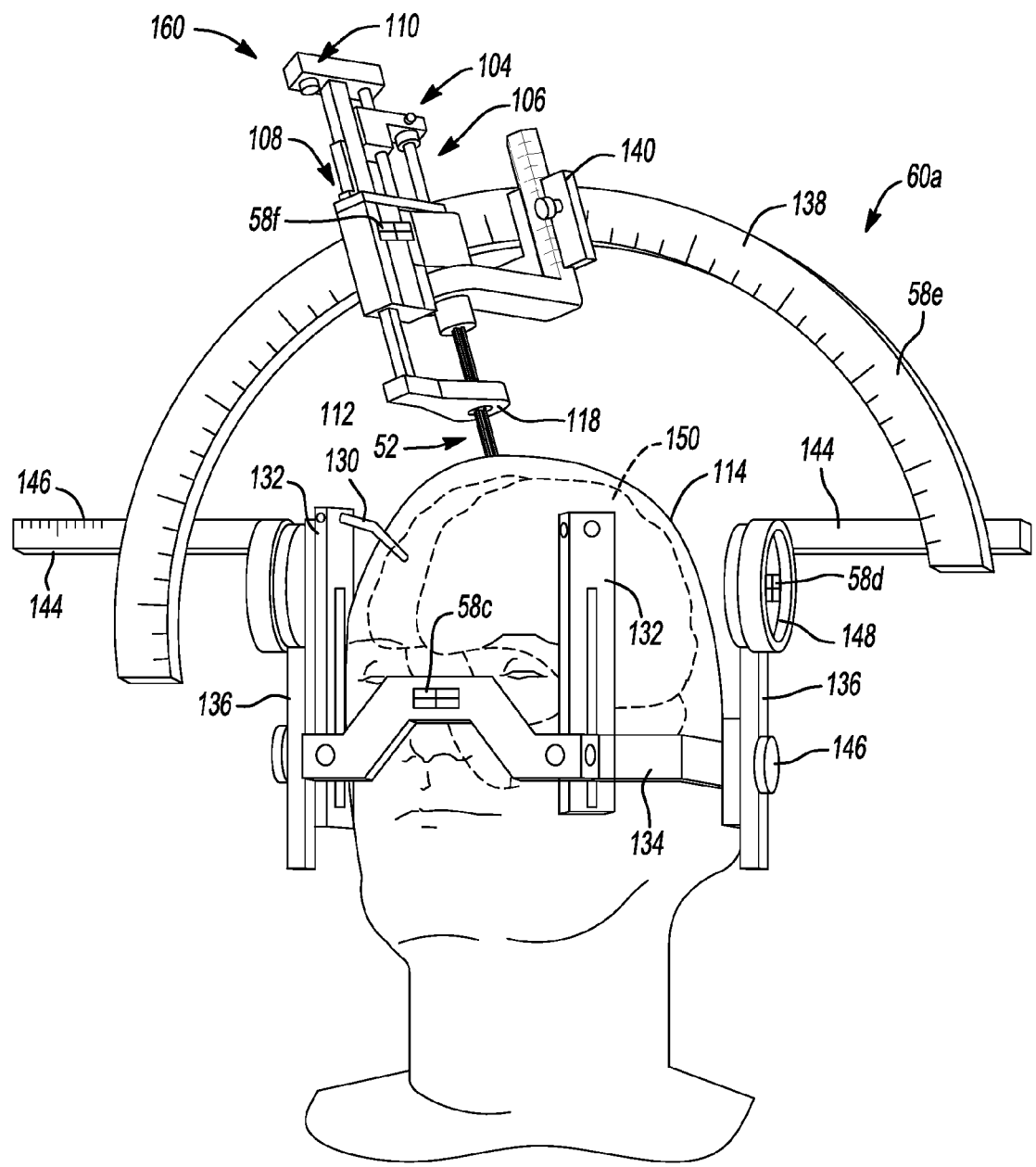
FIG. 2 is a detailed perspective view of an exemplary drive system for inserting one or more test electrodes into an anatomy according to various embodiments of the present disclosure.
Figure 3:
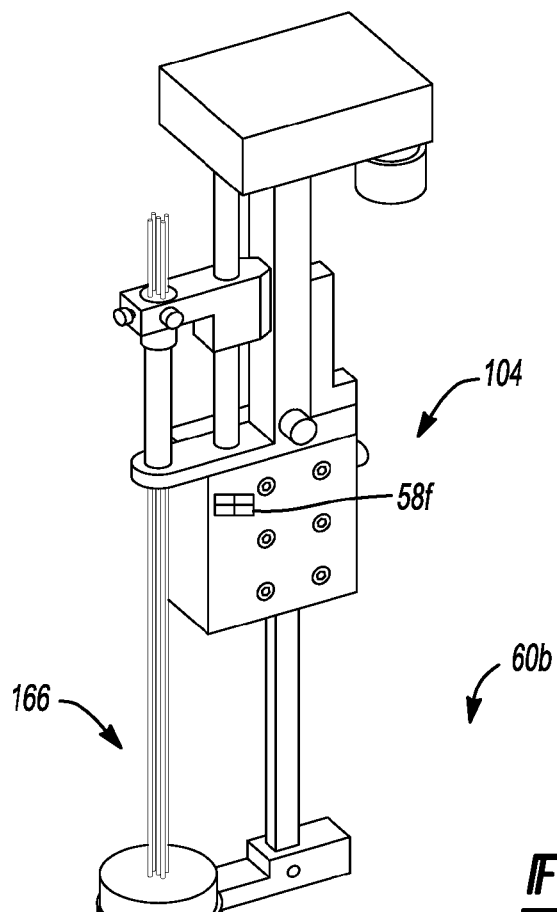
FIG. 3 is a detailed perspective view of an exemplary drive system for inserting one or more test electrodes into an anatomy according to various embodiments of the present disclosure.

With continued reference to FIG. 1 and with additional reference to FIGS. 2 and 3, a guide or drive system 104 for use with an exemplary head frame 60, such as a stereotactic head frame 60a (FIG. 2) or a small-scale head frame 60b (FIG. 3) is illustrated. The drive system 104 can be used to drive various instruments, such as ME and a macroelectrode into an anatomy, such as the brain. As will be discussed in more detail herein, a procedure on the brain can include a recorder for detecting electrical activity in the brain with the ME. Once a recording of the brain has occurred, a macroelectrode can be delivered to an area identified with the ME. Generally, the ME, which can be used to identify a selected region of the brain is removed and the macroelectrode is driven and guided along a similar or identical trajectory or axis relative to the removed ME. The macroelectrode can be provided to electrically stimulate the selected region of the anatomy, either short term or long term.

The drive system 104 can include any appropriate drive system. The drive system 104 can include a driven or control portion 106, a connector rod or support portion 108, a drive portion 110 and a guide system 112. The driven portion 106, support portion 108 and drive portion 110 of the drive system 104 can comprise the microTargeting Drive® system produced by Fred Haer Corp., FHC Inc., 1201 Main Street, Bowdoinham Me. 04287, USA. The drive system 104, can be interconnected with various guide or support portions, such as the stereotactic head frame 60a, small-scale head frames, robotic devices, or guide devices, to drive various instruments into selected portions of the anatomy. Various adapters can be used to connect the drive system to the selected support portions, including those sold by FHC, Inc. For example, the drive system 104 can be interconnected with the head frames 60 to position the drive system 104 at an appropriate location to drive various instruments 52 into a cranium 114. The instruments 52 to be driven with the drive system 104 can include any appropriate instruments, including those examples discussed further herein. For example, the drive system 104 can drive ME, DBS probes, macroelectrode stimulators, or other appropriate instruments.

The drive system 104, in use, can be used to drive or move selected instruments 52 with the driven portion 106 based on torque received from the drive portion 110. The drive portion 110 can be electrically or manually powered to drive an instrument holding section 106a. The support portion 108 can hold each of the portions of the drive system 104 during operation. The guide system 112 can cooperate with the drive portion 106 of the drive system 104 to drive the selected instruments 52 into the appropriate portion of the anatomy, such as the cranium 114. One skilled in the art will understand that various gear trains and tracks can be used to transfer a force from the drive portion 110 to the holding section 106a.

The guide system 112 can be the guide system as disclosed in commonly owned U.S. patent application Ser. No. 11/733, 362 (unofficial), filed Mar. 10, 2007 (unofficial), entitled "System For Guiding Instruments Having Different Sizes," hereby incorporated by reference in its entirety, the guide system 112 will not be described in great detail herein. Briefly, however, the guide system 112 can include an instrument guiding system or portion 118 that can define one or more guide bores. The guide bores can be formed in the guiding system 118 to guide a selected instrument 52 having a selected dimension. For example, the guide bore can include a diameter that allows for appropriate guiding of a relatively large instrument, such as a DBS probe or lead, as will be discussed in greater detail herein.

The drive system 104 can be interconnected or associated with the stereotactic head frame 60a as illustrated in FIG. 2. As the stereotactic head frame 60a can be any suitable stereotactic head frame known in the art, such as the Leksell Stereotactic System® provided by Elekta AB, the stereotactic head frame 60a will not be discussed in great detail herein. Briefly, however, the stereotactic head frame 60a can include various components that are interconnected with the cranium 114. The stereotactic head frame 60a can be interconnected to the cranium 114 using various connection portions including fixation pins 130 that extend from connector or positioning arms 132. The stereotactic head frame 60a can further include a positioning ring 134, placement arms 136, an arcuate placement track or track 138 and a slide 140. The positioning arms 132, can be fixed to the cranium 114 with the fixation pins 130. The positioning arms 132 can be interconnected with the positioning ring 134 at a second end. The positioning ring 134 can include areas to interconnect a plurality of the positioning arms 132 therewith.

Extending from the cranium 114 can be the placement arms 136. The placement arms 136 can be interconnected with the track 138, via connecting arms 144. The connecting arms 144 can be moved relative to the positioning ring 134, via a first connection mechanism 146. The connecting arms 144 can be positioned relative to the placement track 142, via a second connection system 148. The placement track 142 can also be moveably connected to the connecting arms 144 in any appropriate manner. Therefore, the positioning ring 134 can be fixed to the cranium 114 and the placement track 142 can be positioned relative to the cranium 114 using the plurality of connection system 146, 148 and any other appropriate connection mechanism.

The slide 140 can be moved along the track 138 to achieve a selected placement of the slide 140. As illustrated, the track 138 can include calibrated marks for determining a position of the slide 140 relative to the track 138. The connecting arms 144 can also include calibrated marking 144a. The drive system 104 can be interconnected with the slide 140 so that it can be moved relative to the cranium 114 of the patient 12. As one skilled in the art will understand, the slide 140 can be positioned relative to the cranium 114 in a substantially planned manner or selected manner so that the instruments 52 can be driven into the cranium 114 along a selected path. The selected path can ensure the positioning of the instruments 52 in a selected position within the cranium 114. As one skilled in the art will further understand, the path or trajectory of the instruments 52 can be selected based upon a selected final position of the instruments 52 within a brain 150 of the patient 12.

The stereotactic head frame 60a can be positioned by optionally using the navigation system 10, or various other navigation systems, such as that discussed further in U.S. patent application Ser. No. 10/651,267 (now U.S. App. Pub. No. 2005/0049486), entitled "Method and Apparatus for Performing Stereotactic Surgery," incorporated herein by reference. Various tracking devices 58 can be interconnected with the stereotactic head frame 60a such as a first tracking device 58c positioned on the positioning ring 134, a second tracking device 58d positioned on the second connection system 148, a third tracking device 58e positioned on the track 138, and a fourth tracking device 58f positioned on the slide 140 or the drive system 104. The various tracking devices 58c-58f can be used with the tracking system 44 to determine a position of each of the components of the stereotactic head frame 60a, and to determine a position of the slide 140 and/or the drive system 104 relative to the cranium 114. It will be understood, however, that any appropriate stereotactic head frame 60a, either navigated or not, can be used with the drive system 104. In addition the various tracking devices 58c-58f can be any appropriate type or be used with any appropriate system, such as optical electromagnetic, acoustic, accelerometer, etc.

According to various embodiments, the drive system 104 can be interconnected to a smaller support mechanism or small-scale head frame 60b, as illustrated in FIG. 3. The small-scale head frame 60b can be any appropriate mechanism, such as the NEXFRAME™ sold by Image Guided Neurologics of Florida, USA or Medtronic, Inc. of Minnesota, USA. The small-scale head frame 60b can include the drive system 104 interconnected therewith. Also, movement of the drive system 104 can be allowed relative to the cranium 114 to ensure an appropriate or selected position of the drive system 104 relative to the cranium 114.

The small-scale head frame 60b can include a base 400 that is fixedly connected to the cranium 114 of the patient 12. The base 400 can define an aperture or opening 402 that allows the instruments 52 to pass through the base 400 into the cranium 114. A moveable base 404 can be interconnected to the base 400 and the drive system 104 can be connected to the moveable base 404. Various set or locking screws 406 can be used to fix the moveable base 404 to a selected position. Further, various markings can be provided on the moveable base 404 or the fixed base 400 to assist in obtaining a selected orientation of the moveable base 404 to the cranium 114.

Further, various tracking devices can be interconnected with the small-scale head frame 60b. For example, a fifth tracking device 58g can be interconnected with the fixed base 400. A sixth tracking device 58h can be interconnected with the moveable base 404. The sixth tracking device 58h can also be used to determine the position of the moveable base 404 relative to the fixed base 400 and the cranium 114. Again, the fourth tracking device 58f can be interconnected with the drive system 104 to determine a position of the drive system 104 relative to the small-scale head frame 60b. The various tracking devices 58g-h can be used with an optional tracking and navigation system, such as the tracking system 44 and navigation system 10, to determine a position of the various components of the small-scale head frame 60b or the drive system 104 relative the cranium 114 and the brain 150, as further discussed herein.

The various components of the drive system 104 and the stereotactic head frame 60a or the small-scale head frame 60b can be provided to allow for efficient sterilization or sterile use. The stereotactic head frame 60a can be formed of sterilizable materials. The stereotactic head frame 60a, therefore, can be removed after a procedure, cleaned and sterilized for additional procedures. The stereotactic head frame 60a can also be formed of a single use material, either a metal, ceramics, or polymers, but are not limiting to the present teachings. Also, the small-scale head frame 60b can be formed of a rigid polymer to provide for a substantial single use device. Alternatively, the small-scale head frame 60b can be formed of a metal, metal alloy, ceramics, or polymers, but are not limiting to the present teachings, that can also be used for multiple procedures.

As illustrated in FIGS. 2 and 3, the drive system 104 can be used to guide one or more exemplary instruments 52, such as one or more cannulated electrode systems 160, into the brain 150. The cannulated electrode system can include one or more members that include a through passage or cannula member. The cannulated electrodes 160 can be used to record activity in the brain 150 and to accurately identify a portion of the brain 150 for stimulation in a first position, and in a second position, a selected one of the cannulated electrodes 160a can be used to stimulate the selected portion of the brain 150. As each of the cannulated electrodes 160 can be substantially similar, only one of the cannulated electrodes 160 will be discussed in great detail in reference to FIGS. 4-6, and the same reference numbers will be used to denote the same or similar components on the remaining plurality of cannulated electrodes 160a-160e, in FIGS. 8A-8C. The cannulated electrode 160 can include an insertion cannula 162, a macroelectrode 164, a microelectrode 166, and an indicator 168.

With reference to FIGS. 4-6, the insertion cannula 162 can comprise an outer surface 170 and an inner bore 171. The insertion cannula 162 can be comprised of a non-electrically conductive material, such as a non-conductive polymer, metal or metal alloy, for example. The outer surface 170 of the insertion cannula 162 can be gripped by the guide system 112 to drive the cannulated electrodes 160 into the anatomy. For example, the outer surface 170 can include a grip 172 at a first end 173 that can have a greater thickness T than a remainder of the outer surface 170 to provide a surface to which the guide system 112 can be coupled. Thus, the grip 172 can enable the guide system 112 to drive the cannulated electrodes 160 into the anatomy. A second end 174 of the insertion cannula 162 can include a tip 174a. The inner bore 171 can be defined from the first end 173 to the second end 174, and can be sized to slideably couple or retain the macroelectrode 164 and the microelectrode 166 within the insertion cannula 162.

The macroelectrode 164 can be slideably coupled to the insertion cannula 162. The macroelectrode 164 can include an insulation layer 180, a proximal end 182, a distal end 184 and an inner bore 186. The macroelectrode 164 can transmit or carry a current from a connector or pin 188 to stimulate the anatomy, as will be discussed herein. The insulation layer 180 can form an exterior surface of the macroelectrode 164 to prevent the electric charge from being transmitted to the insertion cannula 162. Stimulation to the brain 150 occurs when the current is transferred to the brain 150 from the uninsulated portion 165. Briefly, ground can be provided via a connection to the insertion cannula 162 that is electrically coupled near the macroelectrode 164 and the microelectrode 166. It will be understood, that multiple insulation layers 180 could be coupled to any of the insertion cannula 162, macroelectrode 164 and the microelectrode 166, if desired.

The proximal end 182 of the macroelectrode 164 can be coupled to the indicator 168, as will be discussed. The proximal end 182 can also be positioned relative to the insertion cannula 162 such that the proximal end 182 can be gripped by the user 39 to retract the macroelectrode 164 within the insertion cannula 162, if desired, as will be discussed herein (FIG. 5). The proximal end 182 can also include a stop 190 (FIG. 6). The stop 190 can have a diameter larger than a diameter of the inner bore 171 of the insertion cannula 162 to prevent the macroelectrode 164 from being extended too far into the cranium 114, as will be discussed herein. In addition, the connector 188 can be coupled to the proximal end 182 of the macroelectrode 164 near the stop 190.

The distal end 184 of the macroelectrode 164 can comprise an angled tip 184a to act as a trocar to gradually engage the anatomy, such as the brain 150, as the macroelectrode 164 is driven into the anatomy in the first position and second position. A tip of the macroelectrode 164, including the angled tip 184A, can be provided to occlude a portion or opening of the insertion cannula 162. The insertion cannula can include an internal diameter defined by the inner surface 171 of the insertion cannula. The occlusion of the internal diameter of the insertion cannula 162 with the macroelectrode 164, can substantially minimize the open internal diameter of the insertion cannula 162. As discussed above, the micro-electrode 166 includes a substantially small diameter, and the open diameter of the macroelectrode 164 can be substantially inconsequential when engaging the brain 150. As discussed herein, the selected occlusion of the insertion cannula 162 can be used to eliminate or minimize material entering the internal diameter of the insertion cannula 162. The inner bore 186 can be defined from the proximal end 182 to the distal end 184. The inner bore 186 can be sized to receive the microelectrode 166 therethrough.

Figure 8A:
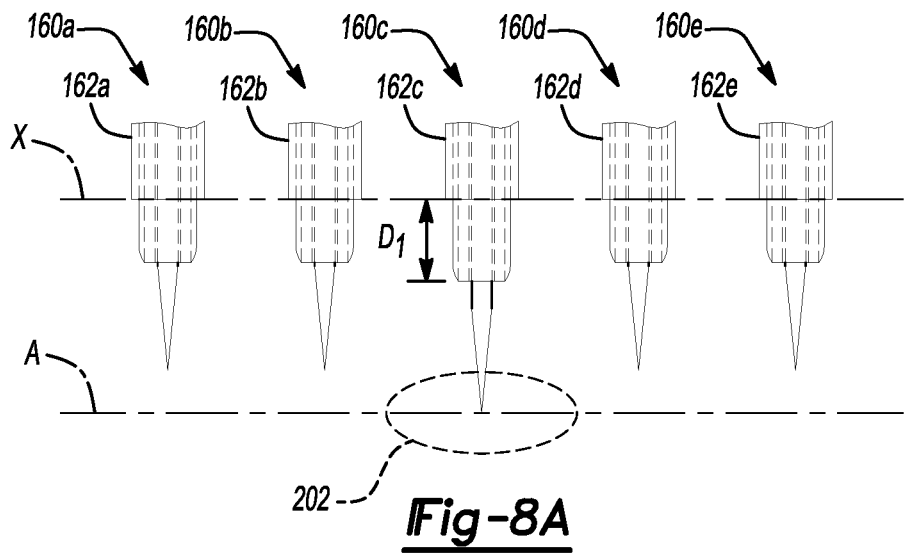
FIG. 8A-8C is a schematic view of a process of positioning electrodes and material relative to a selected region.

The microelectrode 166 can be slideably coupled to the macroelectrode 164. The microelectrode 166 can include a proximal end 192 and a distal end 194 (FIG. 6). The proximal end 192 of the microelectrode 166 can be coupled to an electrical connector 198. The connector 198 can be in communication with a sensor system to receive and interpret or display a received potential or current from the brain 150. The distal end 194 of the microelectrode 166 can define a tip 194a with no insulation. The tip 194a can contact the brain 150 in the first position to record activity in the brain 150 as shown in FIG. 3 and FIG. 8A. In the second position, the tip 194a can be retracted within the macroelectrode 164 as shown in FIG. 5A-B and FIGS. 8B-8C.

The indicator 168 can provide an indication if the macroelectrode 164 is in the second position. In this regard, the indicator 168 can be coupled to the proximal end 182 of the macroelectrode 164 to indicate a position or depth of the distal end 184 of the macroelectrode 164 relative to the insertion cannula 162. Generally, in the second position, as shown in FIG. 5A the macroelectrode 164 of the selected one of the plurality of cannulated electrodes 160a can be fully extended so that this selected macroelectrode 164a can stimulate the brain 150. Thus, the macroelectrode 164 of a selected one of the plurality of cannulated electrodes 160, can be extended a first distance D1 relative to the insertion cannula 162a of the selected cannulated electrode 160a. For example, the first distance D1 can be about 1 millimeters (mm) to about 10 centimeters (cm), including about 18 mm.

Figure 8B:
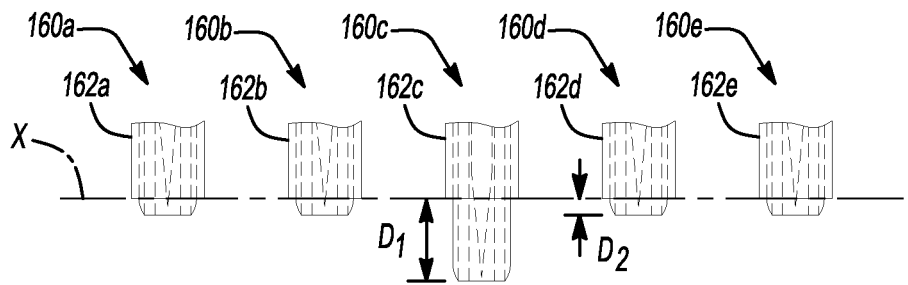
Figure 8C:
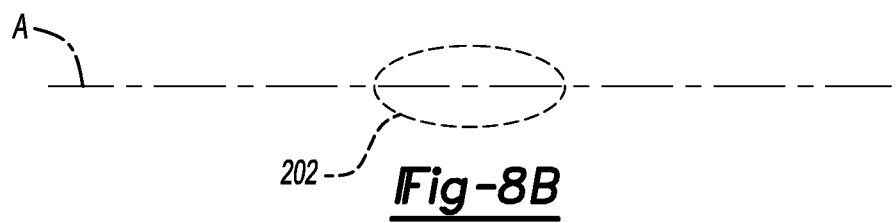

The macroelectrodes 164 of the remaining plurality of cannulated electrodes 160 can be retracted to or only extend a second distance $D_2$ relative to the insertion cannulas 162 of the remaining cannulated electrodes 160 FIGS. 5B and 8B-8C. The second distance $D_2$ can be less than the first distance $D_1$ to ensure that only the macroelectrode 164 of the selected cannulated electrode 160a contacts a selected portion 202 within the brain 150 to stimulate the brain 150. For example, the second distance $D_2$ can be about 0.01 mm to about 10 mm, such as about 2 mm to about 5 mm, and can include about 3 mm. As discussed herein, the distances $D_1$ and $D_2$ can be relative to the insertion cannula 162. The insertion cannula 162 can be inserted a selected distance into the brain such as about 2 cm to about 10 cm, including about 6 cm to about 8 cm, such as about 7 cm. The distance of the insertion cannula 162 is generally from a surface of the brain 150.

The indicator 168 can comprise a visual indicator, an audible indicator, a tactile indicator or a combination thereof that can indicate whether the remaining macroelectrodes 164 are extended the second distance beyond their respective insertion cannulas 162 in the second position and if the macroelectrode 164 of the selected one of the cannulated electrodes 160 is extended the first distance $D_1$, as illustrated in FIGS. 8B and 8C. For example, the indicator 168 can comprise a visual indicator, such as a marking or visual indicia 168a applied to the insulation layer 180 on the proximal end 192 of the macroelectrodes 164, as shown by cross-hatching in FIG. 5B. The visual indicia 168a can be formed on the proximal end 192 of the macroelectrodes 164 by any suitable technique, such as painting, taping, dyeing, coating, etc., and in addition, can comprise any suitable indicia, such as solid, striped, dashed, dotted, etc. It will be understood that the visual indicia 168a can include a layer of material added to the exterior of the macroelectrode 164 or can be incorporated into the insulation on the macroelectrode 164. In any embodiment, the indicator 168 can be formed to allow movement of the macroelectrode 164 relative to the insertion cannula 162.

With a visual indicator 168, the user 39 can visually confirm, based on whether the visual indicia 168a is visible, not visible, or the amount of the visual indicia 168a visible, if the remaining macroelectrodes 164 are in the second position from the insertion cannula 162, and if the macroelectrode 164 of the selected cannulated electrode 160 is in the first position. In this example, the visual indicia 168a can extend a length L along the proximal end 182 of the macroelectrode 164 that is equal to the distance required to retract the macroelectrodes 164 such that the macroelectrodes 164 are spaced the second distance $D_2$ from the insertion cannulas 162, and thus, the length L of the visual indicia 168a can comprise the difference between the first distance $D_1$ and the second distance $D_2$.

The visual indicia 168a can also include various attributes. For example, the visual indicia can include a plurality of colors or gradations of colors to indicate the amount of distance traveled or whether the selected position of the macroelectrode 164 has been achieved. For example, the indicia 168a can include a first color, a second color, and a third color. Each of the three colors can extend a selected distance, such as 5 mm along the overall length L. The three different colors can indicate to the user 39 when a first 5 mm, a second 5 mm, and a third 5 mm has been traveled. Further, the various colors can indicate to the user 39 how close to the final position of the macroelectrode it is to achieving its final position. Also, the visual indicia can include calibrated indicia, such as mm markings.

Moreover, as briefly discussed above, various other indicia can be used as the indicator 168. For example, the position of the macroelectrode 164 can be tracked with the navigation system 10 to determine whether it has moved the selected distance, such as the length L. Further, potentiometers or switches can be used to determine the amount of movement of the macroelectrode relative to the insertion cannula 162 and the distance can be indicated or displayed on the display device 36. Therefore, it will be understood, that the indicator 168 can be any appropriate indicator to be used by the user 39 to determine whether the macroelectrode 164 has moved the length L relative to the insertion cannula 162.

With reference now to FIG. 7, a flowchart 298 illustrates an exemplary method that can be used to control the movement of the cannulated electrodes 160 and insertion and withdrawal of the macroelectrode or DBS 164 and the ME 166. FIGS. 8A-8C illustrate schematically the process of the flow chart 298. It should be noted, however, that the foregoing example is merely exemplary, and the technique for the insertion and withdrawal of the cannulated electrodes 160 could be employed with any suitable method in which it is required to retract an instrument that is retained within another instrument. In the case of performing a procedure on an anatomy, such as the brain 150, with reference to FIG. 7, at block 300, a securement device can be attached to the patient 12. The securement device can comprise a head frame, such as the stereotactic head frame 60a or the small-scale head frame 60b, however, the securement device could comprise a robotic arm (not shown).

Next, at block 302, the drive system 104 can be attached to the securement device. The drive system 104 can be attached with or without the cannulated electrodes 160. At block 304, the drive system 104 can be positioned into the proper position with respect to the anatomy. Thus, if the drive system 104 is coupled to a stereotactic head frame 60a, then the slide 140 can be moved along the track 138 until the drive system 104 is in the desired position. Alternatively, if the optional navigation system 10 is employed, then the navigation system 10 can be used to position the drive system 104 into the proper position even with the use of the head frames 60a, 60b. Further, if a robotic arm is employed to secure the drive system 104 relative to the patient 12, then a controller associated with the robotic arm can be used to drive the robotic arm into the desired position.

Then, with the drive system 104 in the proper position and the cannulated electrodes in the first position, at block 306, the user 39 can drive all of the cannulated electrodes 160 into the anatomy. In the first position, the microelectrode 166 can be extended beyond the macroelectrode 164, and the macroelectrode 164 can be extended beyond the insertion cannula 162 for all of the cannulated electrodes 160a-160e, as illustrated in FIGS. 4 and 8A.

Based on the electric activity recorded by the microelectrodes 166, the user 39 can determine which of the cannulated electrodes 160 is in a best or optimal position for the desired procedure, such as to stimulate a selected region 202 in the brain 150, at block 308. For example, the user 39 will determine that position A is the best position for electrode 160c to stimulate the selected region 202 in the brain 150, according to various embodiments. Though position A is determined with the microelectrode 166 near or at position A, the tip 162a of the insertion cannula 162 is only to position X. Then, the user 39 can position the cannulated electrodes 160 into the second position indicated by block 310. First, the user 39 can retract the microelectrodes 166 of each of the cannulated electrodes 160 at block 312. Second, at block 314, the user 39 can retract the macroelectrodes 164 of all but the selected cannulated electrode 160c until these macroelectrodes 164 are spaced the second distance $D_2$ relative to their respective insertion cannulas 162 (FIGS. 5B and 8B and 8C.) The indicia, such as the visual indicia 168, can indicate to the user 39 that the macroelectrode 164 has been withdrawn a selected distance and to $D_2$.

At decision block 315, the user 39 can determine if the remainders of the plurality of macroelectrodes 164 are retracted to $D_2$ based on the indicator 168. Thus, if the indicator 168 comprises a visual indicator, such as visual indicia 168a, the user can inspect each of the remainder of the plurality of macroelectrodes 164 to ensure each of the remainder of the macroelectrodes 164 is retracted into the second position. Alternatively, if the indicator 168 comprises an audible tone, then the user 39 can ensure that an audible tone has been produced for each of the remainder of macroelectrodes 164. If, for example, the indicator 168 comprises a tactile indicator, then the user 39 can feel each of the remainder of macroelectrodes 164 to determine if the macroelectrodes 164 are in the second position.

Once the distal end 184 of the macroelectrode 164 of the remaining, unselected cannulated electrodes 160, are spaced the second distance $D_2$ from the second end 174 of the respective insertion cannulas 162, (FIG. 8B) the drive system 104 can be actuated to drive all of the cannulated electrodes 160 into the anatomy at block 316. With the cannulated electrodes 160 in the second position, only the macroelectrode 164 of the selected cannulated electrode 160c is positioned at position A to stimulate the selected portion 202 of the brain 150 at block 318. The macroelectrodes 164 of the remaining cannulated electrodes 160 can engage the brain 150 during the stimulation of the brain 150 to prevent "brain shift." In addition, the spacing of the macroelectrodes 164 of the remaining cannulated electrodes 160 the second distance $D_2$ from the insertion cannulas 162 can prevent the second end 174 of the insertion cannulas 162 from contacting the selected region 202 of the brain 150.

According to various embodiments, the selected region of the brain 202 can include an affected or injured portion of the brain. For example, the selected region of the brain 202 can include the sub-thalamic nucleus. One skilled in the art will understand that stimulation of the sub-thalamic nucleus with electrical current can provide relief to symptoms of various illnesses, such as Parkinson's Disease. Moreover, one skilled in the art will understand that the microelectrodes 166a-e can be used to record the activity of various portions in the brain 150 to identify selected neurons or areas of the brain 150. Therefore the microelectrodes 166a-e can be used to identify the selected region of the brain 202, such as the sub-thalamic nucleus.

Moreover, positioning of relatively large volumes of material (i.e. compared to typical dimensions in the brain like the diameter of a brain cell body) within the selected region of the brain 202 can suppress symptoms of the patient 12. Suppression of symptoms with the volume of the cannulated electrodes 160, however, can limit an analysis of the reduction of symptoms induced by the stimulation from the selected macroelectrode 164c. Therefore, withdrawing all but the one macroelectrode 164c, selected for test stimulation, of the macroelectrodes 164 and all the microelectrodes 166 into their respective insertion cannulas 162 to the selected distance $D_2$, can minimize the volume of material introduced into the brain 150. Using the drive system 104 and the process described above an array, such as more than one of the cannulated electrodes 160, can be driven simultaneously into the brain 150. Although multiple cannulated electrodes are moved into the brain 150 only the macroelectrode 164c extends from the insertion cannula 162c to reach the position within the selected region 202 of the brain 150. Once the selected macroelectrode is positioned within the selected region 202 of the brain 150 a stimulation can occur, such as a test stimulation, using electrical current pulses. After successful and satisfactory test stimulation the selected macroelectrode 162c can then be removed and replaced with a chronically implantable macroelectrode or DBS electrode.

Once the test stimulation of the brain 150 is complete, the selected cannulated electrode 160c can be withdrawn from the anatomy at block 320. Then, at block 322, the user 39 can perform the desired therapy. For example, the user 39 can insert a chronically implantable DBS probe, a therapy cannula, an implant, or a radioactive material, along the trajectory defined by the selected cannulated electrode 160c.

Thus, the cannulated electrodes 160 of the present disclosure can enable the user 39 to accurately determine the position of the distal end 184 of each of the macroelectrodes 164 relative to the anatomy. This can enable the user 39 to ensure that the second end 174 of the insertion cannulas 162 may not contact the selected region 202 of the anatomy. Also, positioning the macroelectrode within the insertion cannula 162 can occlude a portion of the cannula 162. As the second end 174 of the open insertion cannulas 162 can be relatively sharp and may damage the anatomy, the placement of the macroelectrodes 164 at the second distance $D_2$ relative to the insertion cannulas 162 can protect the anatomy from the second end 174 of the insertion cannulas 162.

One skilled in the art will understand that the processes and systems discussed above can be used in a surgical procedure. The processes and systems, however, are understood to not be limited to use during or with a surgical procedure. The systems and processes can be used to acquire information regarding inanimate objects, inform or build a database of information; plan a procedure; formulate teaching aids, move selected members relative to any object, etc. In addition, the exemplary description of electrodes and cannulas positioned in the brain 150 is not intended to limit the scope of the invention as it may be used with any appropriate devices to be positioned in any appropriate object.

Registration of image space to physical space can be performed relative to any object in physical space, including a patient, an inanimate object, etc. Also, the registration can occur for any appropriate reason, which may or may not be a surgical procedure.

While specific examples have been described in the specification and illustrated in the drawings, it will be understood, by those of ordinary skill in the art, that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. A system for controlled insertion and withdrawal of at least one electrode in an anatomy comprising:
   at least one insertion cannula that defines a first through passage and a distal end;
   a macroelectrode moveably disposed in the first through passage, the macroelectrode having a proximal end and a distal end, the distal end selectively extendable to a first extended position outside and beyond the distal end of the at least one insertion cannula to engage the anatomy, the distal end also selectively extendable to a second extended position outside and beyond the distal end of the at least one insertion cannula, the distal end of the macroelectrode being extended further away from the distal end of the at least one insertion cannula in the first extended position as compared to the second extended position, the macroelectrode defining a second through passage;
   an insulating member that covers a portion of the macroelectrode and that electrically insulates the macroelectrode from the at least one insertion cannula;
   a microelectrode moveably disposed in the second through passage, the microelectrode having a proximal end and a distal end, the distal end selectively extendable beyond the distal end of the macroelectrode to engage the anatomy; and
   an indicator having a visible marking on the insulating member, the visible marking being a color contrasted from other portions of the insulating member, the visible marking having a length that is substantially equal to a difference in distance between the first extended position and the second extended position, the visible marking being fully blocked by the at least one insertion cannula when the macroelectrode is in the first extended position and the visible marking being fully revealed from the at least one insertion cannula and fully visible when the macroelectrode is in the second extended position such that the indicator indicates only that the macroelectrode is in the first extended position or alternatively in the second extended position.

2. The system of claim 1, comprises a plurality of insertion cannulas and each of the plurality of insertion cannulas include a respective macroelectrode and a respective microelectrode.

3. The system of claim 1, further comprising:
   a drive system coupled to the insertion cannula to move the insertion cannula, the macroelectrode and the microelectrode relative to the anatomy; and
   a frame coupled to the anatomy and the drive system.

4. The system of claim 3, further comprising:
   at least one tracking device coupled to at least one of the frame and the drive system; and
   a navigation system that tracks the at least one tracking device relative to the anatomy during a surgical procedure.

5. The system of claim 4, wherein in the first extended position, the insertion cannula includes the microelectrode extended beyond the distal end of the macroelectrode and the macroelectrode extended beyond the distal end of the insertion cannula such that the microelectrode enters into the anatomy when the drive system moves the insertion cannula.

6. The system of claim 5, wherein in the second extended position, the insertion cannula includes the macroelectrode extended beyond the distal end of the insertion cannula a first distance, and the microelectrode is retracted within the macroelectrode.

7. The system of claim 1, wherein the distal end of the macroelectrode is tapered.

8. The system of claim 1, further comprising a stop that is fixed to the macroelectrode, the stop having a width greater than a diameter of the first through passage to limit movement of the macroelectrode relative to the insertion cannula.

9. A system for controlled insertion and withdrawal of at least one electrode in an anatomy comprising:
   at least one insertion cannula that defines a distal end, a proximal end, and a first through passage that extends through the cannula;
   an electrically conductive macroelectrode slideably disposed in the first through passage, the macroelectrode having a proximal end and a distal end, the distal end selectively extendable to a first extended position outside and beyond the distal end of the at least one insertion cannula to electrically communicate with the anatomy, the distal end selectively extendable to a second extended position outside and beyond the distal end of the at least one insertion cannula to substantially occlude the first through passage for gradually engaging the anatomy as the macroelectrode and insertion cannula are advanced relative to the anatomy, the distal end of the macroelectrode being extended further away from the distal end of the at least one insertion cannula in the first extended position as compared to the second extended position, the macroelectrode defining a second through passage that extends through the macroelectrode;
   an insulating member that covers a portion of the macroelectrode and that electrically insulates the macroelectrode from the at least one insertion cannula;
   an electrically conductive microelectrode slideably disposed in the second through passage, the microelectrode having a proximal end and a distal end, the distal end selectively extendable outside and beyond the distal end of the macroelectrode to electrically communicate with the anatomy; and
   at least one indicator having a visible marking on the insulating member, the visible marking being color contrasted from other portions of the insulating member, the visible marking having a length that is substantially equal to a difference in distance between the first extended position and the second extended position, the visible marking being fully blocked by the at least one insertion cannula when the macroelectrode is in the first extended position and the visible marking being fully revealed from the at least one insertion cannula and fully visible when the macroelectrode is in the second extended position such that the indicator indicates only that the macroelectrode is in the first extended position or alternatively in the second extended position.

10. The system of claim 9, comprising a plurality of insertion cannulas each including a respective one of the macroelectrode and a respective one of the microelectrode.

11. The system of claim 10, further comprising:
a drive system coupled to the plurality of insertion cannulas to move the insertion cannulas, the macroelectrodes, and the microelectrodes relative to the anatomy; and
a frame coupled to the anatomy and the drive system.

12. The system of claim 11, further comprising:
at least one tracking device operably coupled to at least one of the frame and the drive system; and
a navigation system that tracks the at least one tracking device relative to the anatomy during a surgical procedure.

13. The system of claim 10, wherein a selected one of the plurality of insertion cannulas in the respective second extended position includes the respective macroelectrode extended beyond the respective insertion cannula a first distance, the respective microelectrode is retracted within the respective macroelectrode for each of the insertion cannulas, and the distal end of the macroelectrode of the selected one extends a second distance beyond each of the insertion cannulas other than the selected one.

14. The system of claim 13, wherein the at least one indicator indicates if the respective macroelectrode of the insertion cannulas other than the selected one are in the second extended position.

15. The system of claim 9, wherein the distal end of the macroelectrode is tapered.

16. The system of claim 9, further comprising a stop that is fixed to the macroelectrode, the stop having a width greater than a diameter of the first through passage to limit movement of the macroelectrode relative to the insertion cannula.

17. A system for controlled insertion and withdrawal of at least one electrode in an anatomy comprising:
at least one insertion cannula that defines a terminal distal end, a terminal proximal end, and a first through passage that extends continuously through the cannula from the terminal proximal end to the terminal distal end;
an electrically conductive macroelectrode slideably disposed in the first through passage, the macroelectrode having a terminal proximal end and a terminal distal end, the terminal distal end being tapered, the terminal distal end selectively extendable beyond the terminal distal end of the at least one insertion cannula to electrically communicate with the anatomy, the macroelectrode defining a second through passage that extends continuously through the macroelectrode from the terminal proximal end to the terminal distal end;
an insulating member that covers a portion of the macroelectrode and that electrically insulates the macroelectrode from the at least one insertion cannula;
an electrically conductive microelectrode slideably disposed in the second through passage, the microelectrode having a terminal proximal end and a terminal distal end, the terminal distal end selectively extendable beyond the distal end of the macroelectrode to electrically communicate with the anatomy;
at least one visible marking on a portion of the insulating member, the visible marking being a color contrasted from other portions of the insulating member to indicate the position of the distal end of the macroelectrode relative to the distal end of the insertion cannula, the at least one visible marking indicating that the distal end of the macroelectrode is in a first extended position extending outside and beyond the distal end of the at least one insertion cannula to electrically communicate with the anatomy, the at least one visible marking indicating that the distal end of the macroelectrode is in a second extended position extending outside and beyond the distal end of the at least one insertion cannula to substantially occlude the first through passage for gradually engaging the anatomy as the macroelectrode and insertion cannula are advanced relative to the anatomy, wherein the distal end of the macroelectrode is extended further away from the distal end of the at least one insertion cannula in the first extended position as compared to the second extended position, the visible marking having a length that is substantially equal to a difference in distance between the first extended position and the second extended position, the visible marking being fully blocked by the at least one insertion cannula when the macroelectrode is in the first extended position and being fully revealed from the at least one insertion cannula and fully visible when the macroelectrode is in the second extended position such that the visible marking indicates only that the macroelectrode is in the first extended position or alternatively in the second extended position;
a stop that is fixed to the macroelectrode, the stop having a width greater than a diameter of the first through passage to limit movement of the macroelectrode relative to the insertion cannula;
a drive system coupled to the at least one insertion cannula to move the at least one insertion cannula, the macroelectrode, and the microelectrode relative to the anatomy;
a frame coupled to the anatomy and the drive system;
at least one tracking device coupled to at least one of the frame and the drive system; and
a navigation system that tracks the at least one tracking device relative to the anatomy during a surgical procedure.

* * * * *